United States Patent
Dellagiacoma et al.

(10) Patent No.: US 12,150,708 B2
(45) Date of Patent: Nov. 26, 2024

(54) DEVICE AND METHOD FOR DETERMINING THE ORIENTATION OF AN OPHTHALMOLOGIC MICROSCOPE DEVICE

(71) Applicant: Haag-Streit AG, Köniz (CH)

(72) Inventors: Claudio Dellagiacoma, Bern (CH); Jörg Breitenstein, Zollikofen (CH)

(73) Assignee: Haag-Streit AG, Köniz (CH)

( * ) Notice: Subject to any disclaimer, the term of this patent is extended or adjusted under 35 U.S.C. 154(b) by 544 days.

(21) Appl. No.: 17/442,989

(22) PCT Filed: Mar. 26, 2019

(86) PCT No.: PCT/EP2019/057631
§ 371 (c)(1),
(2) Date: Sep. 24, 2021

(87) PCT Pub. No.: WO2020/192900
PCT Pub. Date: Oct. 1, 2020

(65) Prior Publication Data
US 2022/0167842 A1 Jun. 2, 2022

(51) Int. Cl.
*A61B 3/00* (2006.01)
*A61B 3/10* (2006.01)
*A61B 3/135* (2006.01)
*A61B 3/14* (2006.01)

(52) U.S. Cl.
CPC .......... *A61B 3/0083* (2013.01); *A61B 3/0008* (2013.01); *A61B 3/1005* (2013.01); *A61B 3/135* (2013.01); *A61B 3/14* (2013.01)

(58) Field of Classification Search
CPC ... A61B 3/0083; A61B 3/0008; A61B 3/1005; A61B 3/135; A61B 3/14
USPC ................................................. 351/200, 205
See application file for complete search history.

(56) References Cited

FOREIGN PATENT DOCUMENTS

| JP | 2004-351151 | 12/2004 |
| JP | 2012-187178 | 10/2012 |
| KR | 2010 0098763 | 9/2010 |
| WO | 98/03113 | 1/1998 |

OTHER PUBLICATIONS

Int'l Search Report (Form PCT/ISA/210) conducted in Int'l Application No. PCT/EP2019/057631 (Jan. 13, 2020).
Int'l Written Opinion (Form PCT/ISA/237) conducted in Int'l Application No. PCT/EP2019/057631 (Jan. 13, 2020).

*Primary Examiner* — Tuyen Tra
(74) *Attorney, Agent, or Firm* — GREENBLUM & BERNSTEIN, P.L.C.

(57) ABSTRACT

In the device and method, the angle of incidence of slit light onto an eye to be examined is determined from its Purkinje reflection recorded in an image by measuring the offset from the reflection to the apex of the image of the cornea. In another embodiment, Purkinje reflections of light sources arranged around the optical axis of the microscope are correlated with a reference pattern of radial stripes in order to determine the offset between the optical axis and the apex of the eye.

17 Claims, 5 Drawing Sheets

DEVICE AND METHOD FOR DETERMINING THE ORIENTATION OF AN OPHTHALMOLOGIC MICROSCOPE DEVICE

TECHNICAL FIELD

The invention relates to a method for determining an orientation parameter describing at least an aspect of the orientation of at least one component of an ophthalmologic microscope device in respect to an eye to be examined. The invention also relates to an ophthalmologic microscope device having a control unit adapted and structured for carrying out said method.

In this context, the term "orientation" e.g. designates an angle, off-set, or distance between a part of the eye and a part of the device.

BACKGROUND ART

In ophthalmology, certain types of measurements require a good knowledge of the orientation of the device in respect to the eye to be examined.

For example, the quantitative analysis of the sectional view of the cornea as recorded by sending an adjustable slit-shaped beam of light, or slit light, onto the eye from an illumination angle and recording the image from a viewing angle requires knowledge of the angle of incidence of the slit light onto the surface of the eye.

In another example, the analysis of Purkinje reflections in keratometry requires the position of the eye's apex in the recorded image to be known.

DISCLOSURE OF THE INVENTION

The object of the present invention is to provide a method and device of this type that allow the efficient and accurate determination of at least one aspect of the orientation of the ophthalmologic microscope device in respect to the eye.

This object is achieved by the method and device of the independent claims.

Accordingly, in a first aspect, the invention relates to a method for determining an orientation parameter descriptive of the orientation of at least one component of an ophthalmologic microscope in respect to an eye to be examined. The device comprises a microscope, and the method comprises at least the following steps:

Sending light from at least one light source of the device onto the eye.

Viewing the eye through the microscope and recording an image comprising a specular reflection of the light from the eye. In other words, light is reflected from a mirroring surface or interface of the eye (Purkinje reflection), and this light is recorded in an image.

Processing the position of the specular reflection in said image for determining the orientation parameter.

This is based on the understanding that the specular reflection is very sensitive on the orientation of the light source and/or microscope in respect to the eye. Hence, its position in the recorded image is a function of the orientation, and the orientation (or at least one aspect thereof) can be determined by processing the image as claimed.

In particular, the specular reflection is a Purkinje reflection from the anterior surface of the cornea.

In one embodiment, the microscope comprises a slit illumination, and the light source is said slit illumination, i.e. the position of the specular reflection of the light from the slit illumination in the image is processed.

In this case, the method can e.g. be used to
determine the angle of incidence of light from the slit illumination along an illumination direction onto the anterior cornea surface and/or
the angle between a surface normal of the anterior cornea surface and the viewing direction of said microscope.

In particular, the method can in that case comprise the following steps:

Sending slit light from the slit illumination to the eye along an illumination direction.

Viewing the eye with the microscope from a viewing direction: The illumination direction and the viewing directions are different, in particular with an angle of at least 10° between them.

Focusing the microscope onto a curve (location) where the slit light enters the eye while recording said image. This generates, in the image, a picture of the anterior cornea region.

Determining, in the image, the distance between the said curve and the specular reflection.

This is based on the understanding that said distance is a function of the angle of incidence of the slit light onto the anterior surface of the cornea.

Advantageously, the slit light is oriented with its elongate cross sectional axis perpendicular to the illumination and viewing directions.

In another aspect, the light source can be mounted to the microscope, i.e. it is at a fixed, known position in respect to the microscope. In this case, the orientation parameter can e.g. be the position of the apex of the eye in the recorded image because the position of the specular reflection will depend thereon. In this context, "apex" designates the section of the eye's anterior surface extending perpendicular to the optical axis of the microscope.

In this case, advantageously, a plurality of light sources are arranged around the optical axis of the microscope, and the specular reflections of these light sources are recorded in the image. This increases accuracy.

The invention also relates to an ophthalmologic microscope device comprising a microscope, at least one light source, a camera mounted to the microscope, and a control unit. The control unit is adapted and structured for carrying out the method as described herein.

The invention is particularly suited for determining the thickness of the cornea and/or the curvature of the anterior surface of the eye.

BRIEF DESCRIPTION OF THE DRAWINGS

The invention will be better understood and objects other than those set forth above will become apparent when consideration is given to the following detailed description thereof. This description makes reference to the annexed drawings, wherein.

MODES FOR CARRYING OUT THE INVENTION

Figure 1:
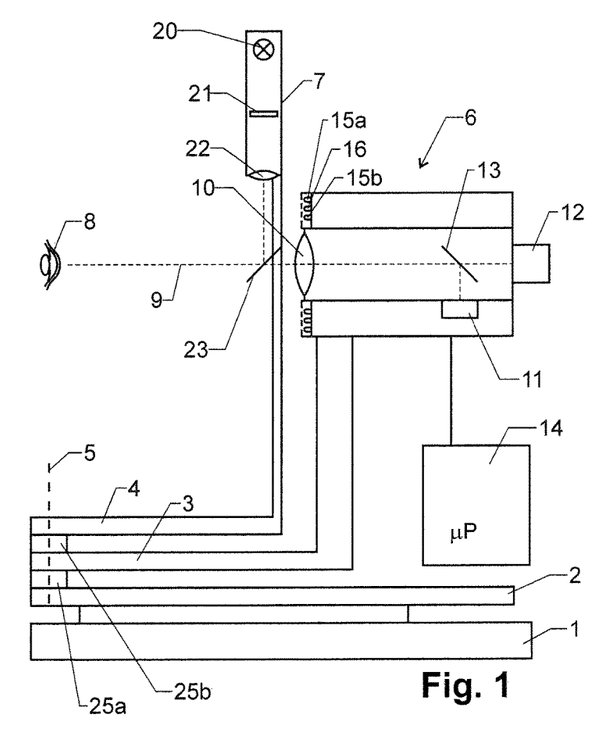
FIG. 1 shows a lateral view of a slit lamp microscope.
Figure 2:
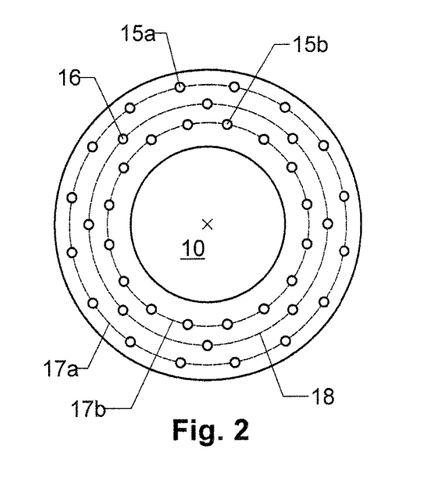
FIG. 2 shows a front view of the microscope as seen from the eye to be examined.
Figure 3:
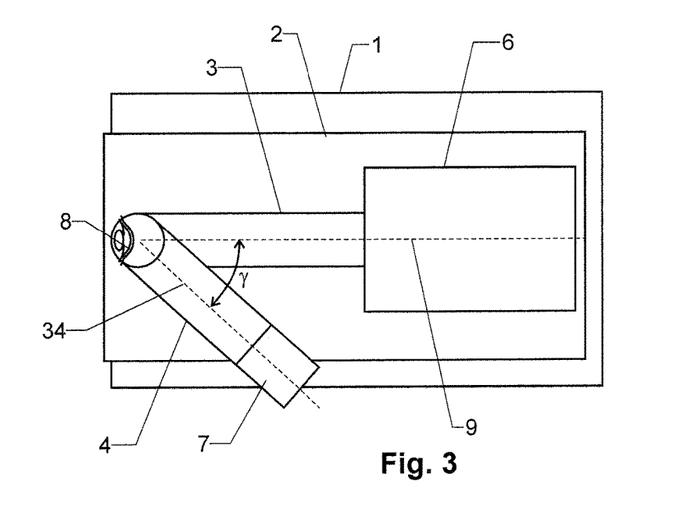
FIG. 3 shows a top view of the microscope (with the slit lamp arm pivoted by an angle γ in respect to the microscope's optical axis)

Device:

FIGS. 1-3 show an embodiment of a device designed as a slit lamp microscope. The device comprises a base 1 resting e.g. on a desk, a horizontally and vertically displaceable stage 2 mounted to base 1, a first arm 3, and a second arm 4.

The arms 3 and 4 are mounted to stage 2 and pivotal about a common vertical pivot axis 5.

The device may further include a headrest mounted to base 1 for receiving the patient's head.

Arm 3 carries a microscope 6 and arm 4 a slit illumination 7.

Slit illumination 7 is optional. It may e.g. be a conventional slit lamp as known to the skilled person, adapted to project a slit-shaped light beam onto the eye 8 to be examined.

Microscope 6 has an optical axis 9 intersecting with pivotal axis 5. It may comprise an entry objective 10 forming part of conventional, non-telecentric imaging optics, which projects an image of eye 8 onto a camera 11 and/or an eyepiece 12.

For quantitative measurements, the device advantageously is equipped with camera 11, while eyepiece 12 is optional. A beam splitter 13 may be arranged to spilt light between these components.

A plurality of first light sources 15a, 15b and second light sources 16 may be arranged on microscope 6 and movable together with it. Advantageously, they are located around entry objective 10 and/or on a side of microscope 6 that faces eye 8.

The light sources 15a, 15b, 16 may be arranged radially outside entry objective 10. This simplifies the design of the device.

In the present embodiment, the first light sources 15a, 15b are arranged on at least a first circle 17a and a second circle 17b, with at least three of the first light sources on each circle.

The second light sources 16 are arranged on a third circle 18, with the circle 18 arranged advantageously between the circles 17a, 17b of the first light sources 15a, 15b.

All circles are concentric and perpendicular to optical axis 9 of microscope 6.

In more general terms, a plurality of the first light sources and/or the second light sources are advantageously arranged on at least one circle.

This arrangement in circles simplifies the analysis of the Purkinje reflections and delivers curvature radii of eye 8 in various directions.

In the present embodiment, the first and second light sources 15a, 15b, 16 are point light sources. In particular, the diameter of each first and/or second light source is at least 100 times, in particular at least 1000 times smaller than the distance between eye 8 and microscope 6. Their structure cannot be resolved by microscope 6 even if microscope 6 it is perfectly focused on one of their reflections.

Advantageously, the first and/or second light sources are LEDs. They may, however, also be other types of light sources, e.g. semiconductor lasers.

Advantageously, the first light sources 15a, 15b may be infrared light sources with a wavelength of at least 800 nm.

The second light sources may e.g. have a wavelength of less than 500 nm e.g. emit blue light. Alternatively, they may e.g. emit green or red light.

The device further comprises a control unit 14, e.g. a microprocessor, which is connected at least to camera 11. It may contain a memory with the programming to carry at least part of the processing steps described here and/or the calibration values mentioned below.

Slit illumination 7 comprises a light source 20, a modulator 21 and imaging optics 22.

Modulator 21 is a spatial light modulator defining the cross section of the beam generated by slit illumination 7. It may e.g. be one of the solutions described in U.S. Pat. No. 5,943,118, such as a liquid crystal display or a controllable micro-mirror array.

Imaging optics 22 projects the light from modulator 21 onto the anterior surface of eye 8, e.g. via a mirror 23 mounted to arm 4.

The device may further comprise at least one detector 25a, 25b for detecting the angles of the arms 3 and/or 4 and in particular the angle γ between the optical axis 34 of the slit illumination 7 and the optical axis 9 of the microscope.

Figure 4:
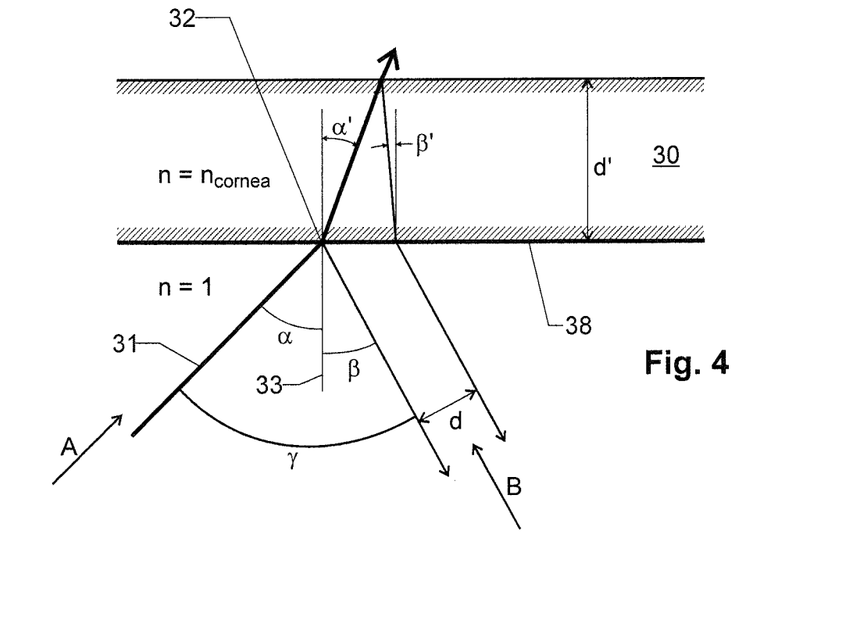
FIG. 4 is a simplified sectional view of the cornea and illustrates the refraction of slit light into the cornea and the recording of its image.
Figure 5:
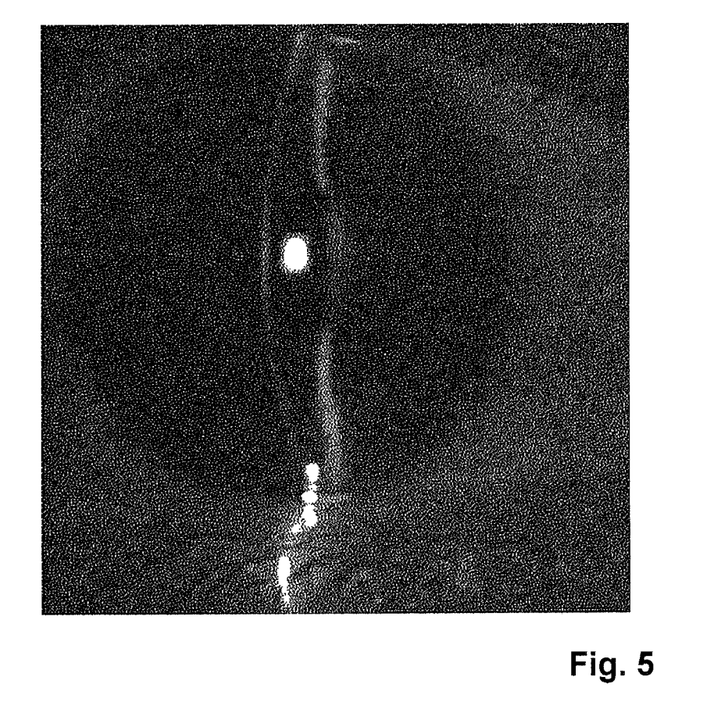
FIG. 5 shows an image recorded by a slit lamp microscope.
Figure 6:
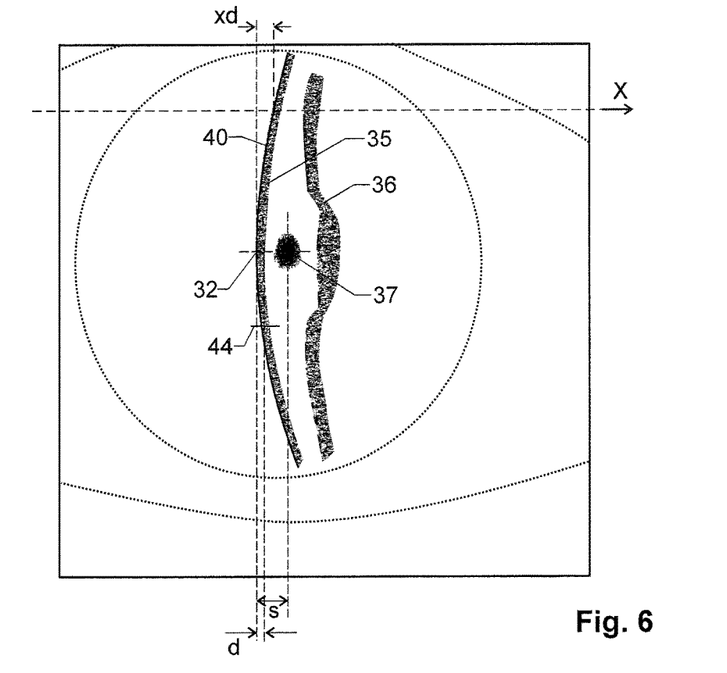
FIG. 6 shows the various elements of the image of FIG. 5 in a more schematic view (inverted, i.e. bright areas appear black)

Cornea Imaging:

A first application of the present device is the recording of cornea images as illustrated in FIGS. 4-6.

FIG. 4 shows an enlarged sectional view of the cornea 30 in a plane perpendicular to pivot axis 5. It is assumed that the slit light 31 from slit illumination 7 has its longest cross-sectional axis parallel to pivot axis 5, such that it appears as a fine line in FIG. 5. It falls on the anterior surface 38 of eye 8 along a curved line, of which a single point 32 is visible in FIG. 4.

Arrow A shows the direction of incidence of the slit light 31 (corresponding to optical axis 34 of slit illumination 7 (cf. FIG. 3).

The angle of incidence of slit light 31 in respect to the surface normal 33 at point 32 is α.

Slit light 31 is refracted into the cornea and crosses the same under an angle α', with $n \cdot \sin(\alpha') = \sin(\alpha)$. n is the mean refractive index of the cornea, which has a typical value of n=1.380.

In FIG. 4, the illuminated cornea is viewed by microscope 6 from a viewing direction B (corresponding to optical axis 9 of microscope 6).

The angle between surface normal 33 and direction B is β.

Again, light going into viewing direction B is refracted at the anterior surface 38 of cornea 30 and has, inside cornea 30, an angle β' with $n \cdot \sin(\beta') = \sin(\beta)$.

FIG. 5 shows the image recorded from viewing direction B by means of camera 11, and FIG. 6 shows the most important components of this image in a more schematic representation.

In particular, it can be seen that cornea 30 forms a curved stripe 35 where slit light 31 is scattered at the cornea's surface as well as at structures within the cornea. When passing deeper into the eye, slit light 31 reaches the iris and lens, which give rise to a further structure 36 in the image.

Further, specular reflection from the anterior surface 38 of the eye typically generates a strong Purkinje reflection 37.

The device can record a plurality of pictures such as those shown in FIGS. 5 and 6, e.g. while moving the slit light. In this manner, a whole region of the eye can be scanned by displacing the slit light along the horizontal direction using the spatial modulator 21.

The width d of the image 35 of the cornea (see FIG. 6) can be used to estimate the thickness d' of the cornea (see FIG. 4). As can be seen from FIG. 4, thickness d' can be calculated from width d using:

$$d' = \frac{d}{\cos(\beta) \cdot (\tan(\alpha') + \tan(\beta'))} \quad (1)$$

In other words, the calculation of the cornea thickness d' requires the knowledge of the angle of incidence α and the angle of observation β in respect to the normal of the eye's anterior surface at point 32.

Since the eye is never perfectly aligned with the microscope and the slit illumination, these angles are usually unknown. The only known angle is the angle γ=α+β between the axes 34 of slit illumination 7 and microscope 6 (cf. FIG. 3), which is e.g. determined using the detectors 25a, 25b.

The following section describes a method to calculate the angle of incidence α (or, equivalently, the angle of observation β).

Angle of Incidence:

The angle of incidence α and the angle of observation β can be determined by analyzing the position of the Purkinje reflection 37 in the image of FIG. 5 or 6.

Figure 7:
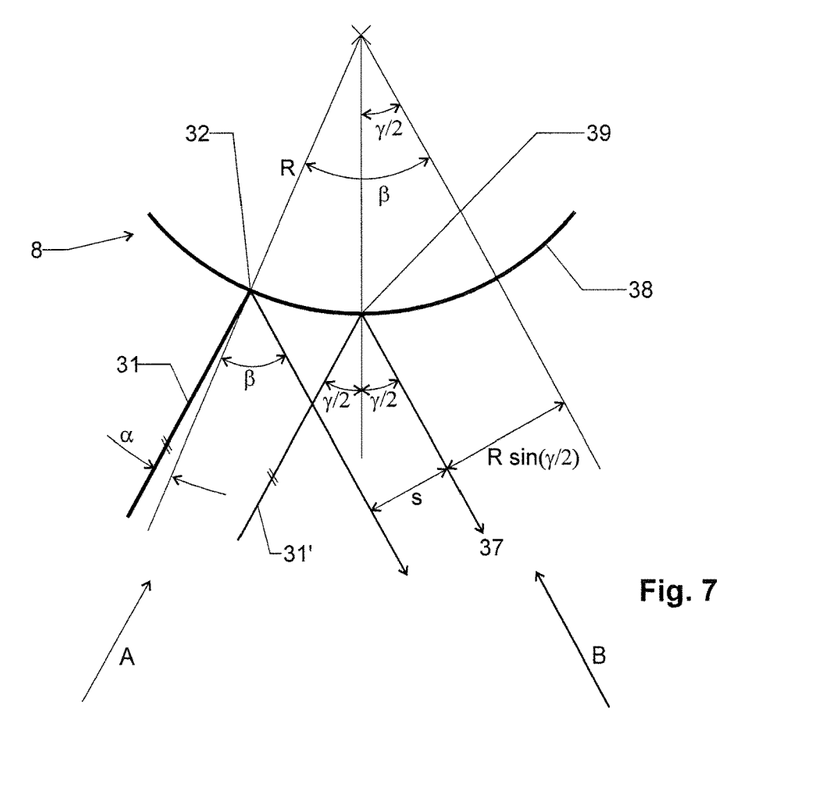
FIG. 7 illustrates the formation of the Purkinje reflection in images of the type of FIGS. 5 and 6.

This Purkinje reflection is generated by specular reflection at the anterior surface 38 of the eye as illustrated by FIG. 7. Namely, it is generated by stray light 31' from slit illumination 7, which is directly reflected by anterior surface 38 into viewing direction B. This takes place at a point 39 of surface 38 where the angle of incidence as well as the angle of reflection is equal to γ/2.

In FIG. 7, it is assumed that slit illumination 7 is far away from the eye such that stray light 31' is substantially parallel to slit light 31.

Microscope 6 is focused on the image of FIG. 6, i.e. on point 32 where slit light 31 enters the eye.

As can be seen in FIG. 7, the image of point 32 is offset from the center of the Purkinje reflection by an offset s. We have $$s + R \cdot \sin(\gamma/2) = R \cdot \sin(\beta) \quad (2)$$

with R being the curvature radius of the eye's anterior surface 38 at points 32, 39.

R can e.g. be assumed to have a typical value of 7.7 mm, or it can be measured using keratometric techniques, such as e.g. described below.

From Eq. (2), the angle of observation β can be calculated as $$\beta = \arcsin\left[\frac{s}{R} + \sin(\gamma)\right]. \quad (3)$$

The angle of incidence α can then e.g. be obtained from $$\alpha = \gamma - \beta. \quad (4)$$

In other words, the analysis of offset s in the recorded image of FIG. 6 allows to determine the angle of incidence α and/or the observation angle β at location 32 where slit light 31 meets anterior surface 38.

This determination may comprise the step of determining the ratio s/R between the offset s and the curvature radius R of the anterior surface of the eye.

Also, the determination may include the step of using the angle γ between the illumination and viewing directions A, B.

The position of Purkinje reflection 37 as well as of point 32 in the image of FIG. 6 can e.g. be determined using known image processing techniques. For example, the recorded image can be correlated with a reference pattern having a typical shape of the Purkinje reflection.

Figure 8:
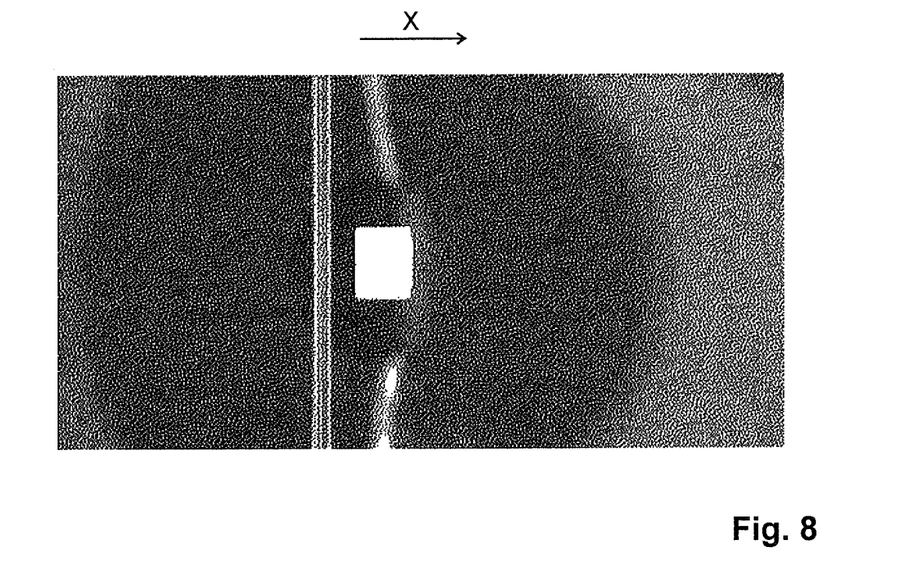
FIG. 8 shows a transformed version of the image of FIG. 5.

Depth Analysis:

In the following, a tool for simplifying the measurement of the depth and/or thickness of anterior eye structures is described. It consists of converting the recorded image of FIGS. 5 and 6 to a transformed image as shown in FIG. 8.

In this method, in a first step, a curve 40 (FIG. 6) representing the location on the image where slit light 31 meets the anterior surface 38 of the eye is determined as described further below.

Based on this curve 40, an offset xd (as shown in FIG. 6) is calculated for each image line. (In this context, each image line e.g. corresponds to a line of pixels perpendicular to pivot axis 5. In FIGS. 5 and 6, these are the horizontal lines of the image.). This offset xd is given by the distance, in image line direction X, between point 32 and curve 40.

Each image line is offset by offset xd along image line direction X, thus moving the pixels corresponding to curve 40 into a single line perpendicular to line direction X. The resulting transformed image is shown in FIG. 8.

In the transformed image of FIG. 8, coordinate X (line direction X) corresponds to the "depth" of an object within the eye.

In more general terms, the depth analysis described above comprises the following steps:

a) Determining a curve 40 in the recorded image that corresponds to the location where the slit light 31 meets the anterior 38 surface of the eye.

b) Offsetting pixel lines in the recorded image along a line direction X by an offset xd, with said line direction corresponding to the direction of a plane including the illumination direction A and the viewing direction B (i.e. line direction X corresponds to the horizontal direction if pivot axis 5 is vertical). For each line, the offset xd corresponds to the distance, in image line direction X, between curve 40 at said line and an apex (point 32) of the curve.

Step b) will result in the image of FIG. 8, where curve 40 is transformed into a straight line.

In above step a), curve 40 needs to be determined. There are various ways to do this, three of which are described in the following:

Curve 40 is advantageously calculated, in approximation, from angle γ between slit illumination axis 34 and optical axis 9 of microscope 6, e.g. assuming that slit light 31 intersects with the center of the curvature of anterior surface 38.

Alternatively, a more refined version of curve 40 may be calculated using the knowledge of the angles α and β as obtained according to the method of the previous section.

Finally, curve 40 may also be calculated by processing the image of FIG. 5 or 6 in finding the edge of cornea region 35.

Cornea Detection:

The position and/or width of the cornea can be detected in the images of FIG. 5, 6, or 8 using image analysis.

Such image detection may e.g. include edge detection techniques.

Figure 9:
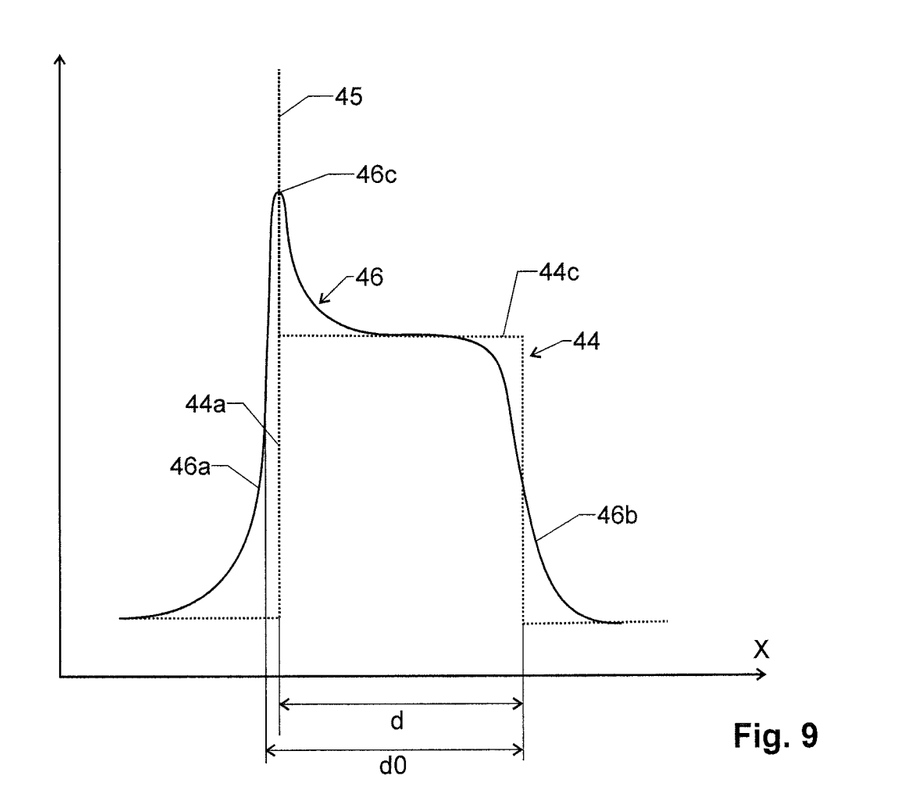
FIG. 9 illustrates the brightness of the light scattered by the cornea.

It must be noted, though, that the light scattering behavior of the cornea is highly asymmetric. This is illustrated in FIG. 9.

In this figure, the dotted line 44 shows the theoretical scattering intensity in a perfect image, along line direction X, for an infinitely narrow slit light. As can be seen, a scattering peak 45 is observed at the location of the cornea's anterior surface. This is due to the strong change of refractive index at the interface between air and the cornea (and its covering tear film).

Within the cornea, scattering is at an approximately constant level 44c. Outside the cornea, scattering is low.

The continuous line 46 shows the effectively observed scattering in the recorded image. It is broadened due to imperfect imaging in the microscope as well as due to the non-zero width of the slit light.

As can be seen, peak 45 leads to the rising flank to be offset away from the theoretical rising flank 44a, i.e. simple edge detection techniques may yield a wrong position for the cornea's anterior surface 38.

Hence, in order to determine the position of the cornea within the recorded image, it is suggested to fit to a parametric model of the brightness to the measured data, which model takes this into account. For example, a model function to be used in a fitting process might e.g. be $$P(x) = A_0 \exp\left(-\frac{(x-x_0)^2}{2\sigma^2}\right) + A_1\left(\text{step}\left(\frac{x-x_0+d}{\sigma}\right) - \text{step}\left(\frac{x-x_0}{\sigma}\right)\right) + k \quad (5)$$

with $$\text{step}(x) = \frac{1 + \tanh(x)}{2}$$

$A_0$ describes the height of the peak 46c, $A_1$ the amplitude at level 44c, $x_0$ the position of the anterior surface and the tear film, d the apparent thickness of the cornea, and $\sigma$ the degree of defocusing and slit light width.

The parameters of the model, such as $A_0$, $A_1$, $x_0$, and $\sigma$ can be determined in the fitting process. For example, nonlinear least-square fitting may be used.

In more general terms, a parametric model P(x; d) of the scattering intensity in the image may be fitted to the image data. The model has a thickness parameter d descriptive of a thickness of the cornea as well was further parameters descriptive of the height, asymmetry and position of the scattering on the cornea. P(x; d) has rising flank 46a and a trailing flank 46b and it has a maximum 46c closer to the rising than the trailing flank. The distance d0 between the steepest part of the rising flank 46a and the trailing flank 46b is larger than the thickness parameter d.

Keratometry:

Another aspect of the technique is now described in an application to keratometric measurements.

Keratometry designates the measurement of the local radius of curvature of the anterior surface of the cornea.

As e.g. described in U.S. Pat. No. 5,790,233, FIG. 1, keratometric measurements can e.g. be based on measuring the Purkinje reflections of light sources.

In the device of FIGS. 1-3, the light sources 15a, 15b, and/or 16 can be used for this type of measurement.

Figure 10:
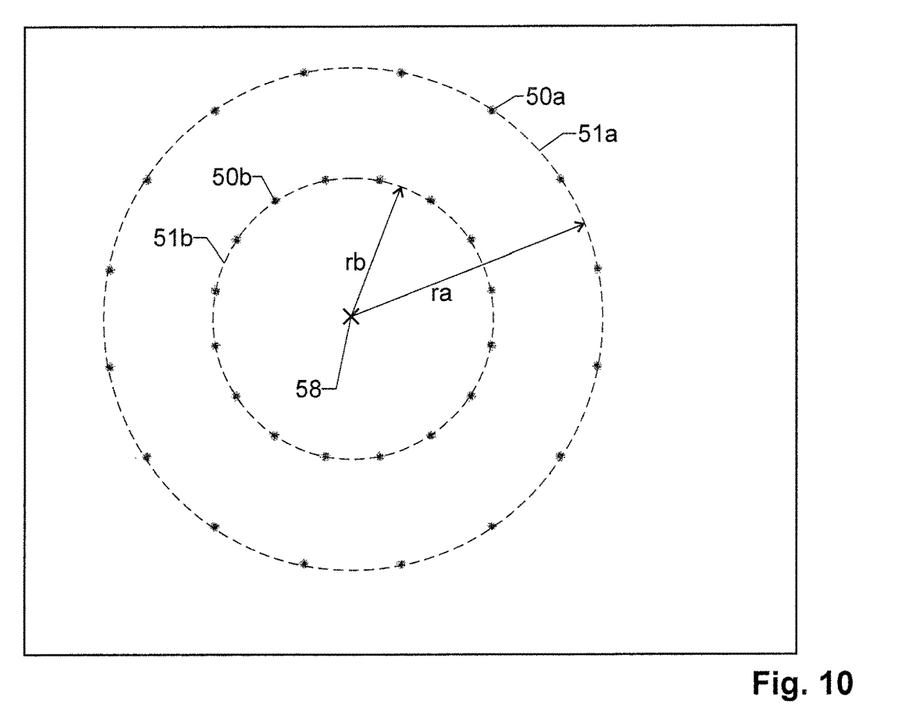
FIG. 10 shows an image of the Purkinje reflections as recorded in a keratometry measurement (dark pixels correspond to bright areas)

For example, the Purkinje reflections 50a, 50b from the light sources 15a, 15b can e.g. be recorded by camera 11 in an image as shown in FIG. 10. The curvature radius r of the eye can then be calculated from one or both of the radii ra, rb of the circles 51a, 51b of the reflections as described in U.S. Pat. No. 5,790,233.

However, as shown in FIG. 10, since the optical axis 9 of microscope 6 may not exactly intersect the apex of the eye and because the curvature of the cornea's anterior surface is not known a priory, the position of the Purkinje reflections 50a, 50b in the recorded image are not known.

Figure 11:
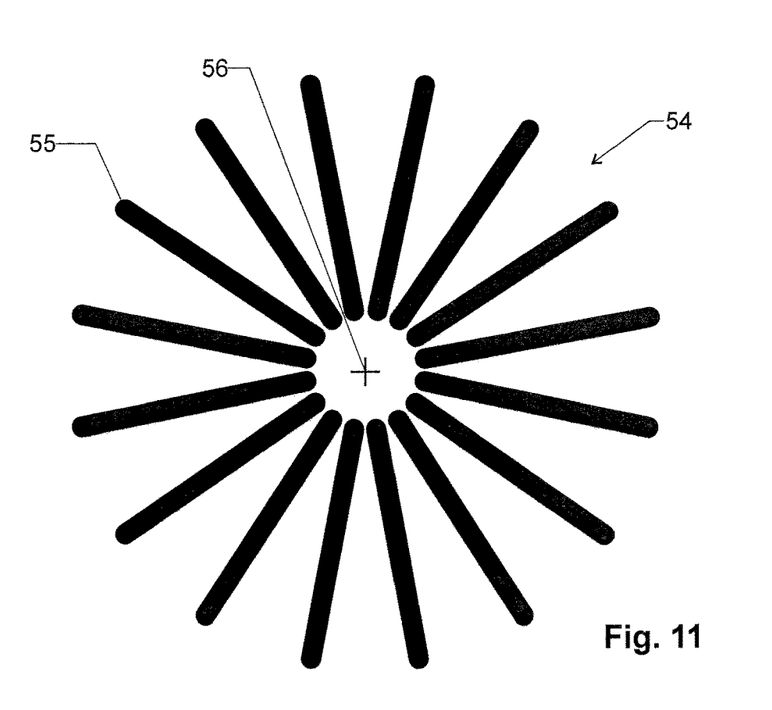
FIG. 11 shows a reference pattern for being used when processing the image of FIG. 10.

In order to determine the center of the circles 51a, 51b, the recorded image is therefore mathematically correlated with a reference pattern 54 as shown in FIG. 11. This reference pattern comprises a plurality of line-shaped regions 55 extending radially from a center point 56. The pixel values at the line-shaped regions 55 differ from those of the background. For example, the pixel values at the line-shaped regions 55 can be set at a first constant value and those of the background at a second constant value.

The peak value of the correlation between the recorded image (FIG. 10) and the reference pattern 54 yields the center 58 of the circles 51a, 51b in the recorded image.

Using a reference pattern of this type has the advantage that the correlation is insensitive to the actual values of the radii ra, rb of the circles 51a, 51b, i.e. to the radius of curvature of the eye and the exact distance between the eye and the microscope.

This method works best if the light sources 15a, 15b used for the keratometry are arranged on at least a first and a second circle 17a, 17b (cf. FIG. 2) concentric to optical axis 9 of microscope 6. For each first light source 15a on the first circle 17a, there is a second light source 15b at a same angular position on the second circle 17b.

The number and/or angular positions of line-shaped regions 55 in reference pattern 54 advantageously correspond to the number and/or angular positions of the light sources 15a, 15b on their circles 17a, 17b.

Once the center 48 of the corresponding circles 51a, 51b in the recorded image is known from the correlation calculation, the position of the Purkinje reflections and/or their distance ra, rb from the center 48 can be calculated, and therefrom the radius of the anterior cornea surface can be calculated.

Notes

As mentioned, the techniques described here allow to determine an orientation parameter describing the orientation of at least one component of an ophthalmologic microscope in respect to an eye to be examined.

In the first examples above, said parameter was the angle of incidence $\alpha$ of the slit light onto the cornea's anterior surface or the angle of observation $\beta$ between the viewing direction and the surface normal at the location of incidence of the slit light.

In the second example above, said parameter was the offset of the microscope's optical axis 9 and the apex of the eye, i.e. the position of center 58 in the recorded image of FIG. 10.

As illustrated by the first example, the microscope does not necessarily have to be focused on the Purkinje reflection used for determining the positional parameter. Rather, it can be focused on other parts of interest, such as the image of the cornea region 35 in FIG. 6.

While there are shown and described presently preferred embodiments of the invention, it is to be distinctly understood that the invention is not limited thereto but may be otherwise variously embodied and practiced within the scope of the following claims.

The invention claimed is:

1. A method for determining an orientation parameter descriptive of an orientation of at least one component of an ophthalmologic slit lamp microscope device comprising a microscope with respect to an eye to be examined, said method comprising:
    sending light from at least one slit illumination light source of the ophthalmologic slit lamp microscope device onto said eye,
    viewing said eye through said microscope and recording an image comprising a specular reflection of said light from said eye, and
    processing a position of the specular reflection in said image for determining said orientation parameter, wherein said orientation parameter is an angle of incidence of light from said slit illumination along an illumination direction onto an anterior cornea surface of said eye and/or wherein said orientation parameter is an angle between a surface normal of said anterior cornea surface and a viewing direction of said microscope.

2. The method of claim 1, further comprising
    sending slit light from said slit illumination to said eye along said illumination direction,
    viewing said eye with said microscope from said viewing direction, with said viewing direction being different from said illumination direction,
    focusing said microscope onto a curve where said slit light enters said eye while recording said image,
    determining, in said image, an offset between said curve and said specular reflection.

3. The method of claim 2, further comprising determining a ratio between said offset and a curvature radius of an anterior surface of said eye.

4. The method of claim 3, further comprising measuring said radius using keratometry.

5. The method of claim 3, further comprising using a typical eye radius for said radius.

6. The method of claim 2, further comprising using an angle between said illumination direction and said viewing direction and said offset for calculating said orientation parameter.

7. The method of claim 2, further comprising
    a) determining a curve in the recorded image corresponding to the location where the slit light meets an anterior surface of the eye, and
    b) offsetting pixel lines in the recorded image along a line direction by an offset, with said line direction corresponding to a direction of a plane including the illumination direction and the viewing direction, wherein, for each line, said offset corresponds to a distance, in said image line direction, between said curve at said pixel line and an apex of said curve.

8. The method of claim 2, further comprising fitting a parametric model P(x; d) to a scattering intensity in the recorded image,
    wherein the model P(x; d) has a thickness parameter d descriptive of a thickness of the cornea as well as further parameters descriptive of a height, asymmetry and position of the scattering intensity,
    wherein said model P(x; d) has rising flank and a trailing flank and it has a maximum closer to the rising than the trailing flank, and
    wherein a distance between a steepest part of the rising flank and a steepest part of the trailing flank is larger than said thickness parameter d.

9. The method of claim 1, wherein said light source is mounted to said microscope.

10. The method of claim 9, wherein said orientation parameter is a position of an apex of said eye in said image.

11. The method of claim 9, wherein a plurality of light sources are arranged around an optical axis of said microscope, wherein said method comprises recording, in said image, the specular reflections of said light sources.

12. An ophthalmologic microscope device comprising:
    a microscope,
    at least one light source,
    a camera mounted to said microscope, and
    a control unit adapted and structured for carrying out the method of claim 1.

13. The method of claim 1, further comprising determining a thickness of a cornea of said eye.

14. A method for determining an orientation parameter descriptive of an orientation of at least one component of an ophthalmologic microscope device comprising a microscope with respect to an eye to be examined, said method comprising:
    sending light from at least one light source of the ophthalmologic microscope device onto said eye,
    viewing said eye through said microscope and recording an image comprising a specular reflection of said light from said eye, and
    processing a position of the specular reflection in said image for determining said orientation parameter,
    wherein said light source is mounted to said microscope,
    wherein a plurality of light sources are arranged around an optical axis of said microscope, wherein said method comprises recording, in said image, the specular reflections of said light sources, and
    mathematically correlating said recorded image with a reference pattern comprising a plurality of line-shaped regions extending radially from a center point.

15. A method for determining an orientation parameter descriptive of an orientation of at least one component of an ophthalmologic microscope device comprising a microscope with respect to an eye to be examined, said method comprising:
    sending light from at least one light source of the ophthalmologic microscope device onto said eye,
    viewing said eye through said microscope and recording an image comprising a specular reflection of said light from said eye, and
    processing a position of the specular reflection in said image for determining said orientation parameter,
    wherein said light source is mounted to said microscope,
    wherein a plurality of light sources are arranged around an optical axis of said microscope, wherein said method comprises recording, in said image, the specular reflections of said light sources,
    wherein said light sources are arranged on at least a first and a second circle concentric to said optical axis, and
    wherein for each light source on said first circle, there is another light source at a same angular positional position on said second circle.

16. The method of claim 15, further comprising determining a curvature radius of an anterior surface of said eye.

17. The method of claim 15, wherein at least one of a number and angular positions of the line-shaped regions in said reference pattern corresponds to the number and angular positions of the light sources on said circles.

* * * * *